United States Patent
Corin

(10) Patent No.: US 9,314,280 B2
(45) Date of Patent: Apr. 19, 2016

(54) MINIMALLY INVASIVE TOOL TO FACILITATE IMPLANTING A PEDICLE SCREW AND HOUSING

(75) Inventor: James Corin, Boulder, CO (US)

(73) Assignee: Zimmer Biomet Spine, Inc., Broomfield, CO (US)

( * ) Notice: Subject to any disclaimer, the term of this patent is extended or adjusted under 35 U.S.C. 154(b) by 512 days.

(21) Appl. No.: 13/540,497

(22) Filed: Jul. 2, 2012

(65) Prior Publication Data

US 2013/0144349 A1 Jun. 6, 2013

Related U.S. Application Data

(63) Continuation of application No. 11/938,073, filed on Nov. 9, 2007, now Pat. No. 8,211,110.

(60) Provisional application No. 60/865,365, filed on Nov. 10, 2006.

(51) Int. Cl.
*A61B 17/70* (2006.01)
*A61B 17/86* (2006.01)

(52) U.S. Cl.
CPC ......... *A61B 17/7076* (2013.01); *A61B 17/7037* (2013.01); *A61B 17/7082* (2013.01); *A61B 17/864* (2013.01); *Y10T 29/49826* (2015.01)

(58) Field of Classification Search
CPC ........... A61B 17/7076; A61B 17/7074; A61B 17/7079; A61B 17/708; A61B 17/7082; A61B 17/7083; A61B 17/7085; A61B 17/8875; A61B 17/8883; A61B 17/8886; A61B 17/8891; A61B 17/8888
USPC ................................ 606/104, 86 A, 916, 914
See application file for complete search history.

(56) References Cited

U.S. PATENT DOCUMENTS

| | | | |
|---|---|---|---|
| 2,990,570 A | 7/1961 | Gilpatrick | |
| 5,530,998 A | 7/1996 | Hurst et al. | |
| 6,004,326 A | 12/1999 | Castro et al. | |
| 6,183,472 B1 | 2/2001 | Lutz | |
| 2004/0039384 A1 | 2/2004 | Boehm et al. | |
| 2004/0144194 A1 | 7/2004 | Allen et al. | |
| 2004/0147937 A1 | 7/2004 | Dunbar et al. | |
| 2005/0065517 A1 | 3/2005 | Chin | |
| 2005/0067815 A1 | 3/2005 | Dearden et al. | |
| 2005/0131408 A1* | 6/2005 | Sicvol et al. | 606/61 |
| 2005/0137593 A1 | 6/2005 | Gray et al. | |
| 2005/0192579 A1* | 9/2005 | Jackson | 606/72 |
| 2005/0228400 A1 | 10/2005 | Chao et al. | |
| 2006/0069391 A1* | 3/2006 | Jackson | 606/62 |
| 2006/0074418 A1 | 4/2006 | Jackson | |
| 2006/0074445 A1 | 4/2006 | Gerber et al. | |
| 2006/0149245 A1* | 7/2006 | Sweeney | 606/61 |

(Continued)

OTHER PUBLICATIONS

Acta Orthop Scand article dated Jun. 1984, by Bostman O. Myllynen P. Riska EB.

*Primary Examiner* — Jerry Cumberledge
(74) *Attorney, Agent, or Firm* — Schwegman, Lundberg & Woessner, P.A.

(57) ABSTRACT

A minimally invasive tool to facilitate implanting a pedicle screw and housing is provided. The minimally invasive tool includes a first sleeve having flexible tabs that couple to a housing and a second sleeve slidably engaged in the first sleeve. The second sleeve provides reinforcing such that the first and second sleeve provide counter torque for driving the pedicle screw.

8 Claims, 7 Drawing Sheets

(56) References Cited

U.S. PATENT DOCUMENTS

| | | |
|---|---|---|
| 2006/0200132 A1 | 9/2006 | Chao et al. |
| 2006/0247630 A1 | 11/2006 | Iott et al. |
| 2006/0247658 A1 | 11/2006 | Pond et al. |
| 2007/0233155 A1* | 10/2007 | Lovell .......................... 606/104 |
| 2009/0143828 A1* | 6/2009 | Stad et al. ................... 606/86 A |

* cited by examiner

MINIMALLY INVASIVE TOOL TO FACILITATE IMPLANTING A PEDICLE SCREW AND HOUSING

PRIORITY UNDER 35 USC §119

The present application claims priority to U.S. Provisional Patent Application Ser. No. 60/865,365, filed Nov. 10, 2006, titled MINIMALLY INVASIVE TOOL TO FACILITATE IMPLANTING A PEDICLE SCREW AND HOUSING, the disclosure of which is expressly incorporated herein by reference.

RELATED APPLICATION

The technology of the present application relates to U.S. patent application Ser. No. 10/915,902, titled Screw and Rod Fixation System, filed Aug. 10, 2004, which is incorporated here by reference.

FIELD OF THE INVENTION

The present invention relates to spinal fixation devices and more particularly to a pedicle screw and rod fixation assembly useful in stabilizing a spine of a patient.

BACKGROUND OF THE INVENTION

Over the years, several techniques and systems have been developed for correcting spinal injuries and/or degenerative spinal processes. Spinal correction frequently requires stabilizing a portion of the spine to facilitate fusing portions of the spine or other correction methodologies. Medical correction of this type is frequently employed for many spinal conditions, such as, for example, degenerative disc disease, scoliosis, spinal stenosis, or the like. Frequently, these corrections also require the use of implants, such as, bone grafts. Stabilizing the spine allows bone growth between vertebral bodies such that a portion of the spine is fused into a solitary unit.

Several techniques and systems have been developed for correcting and stabilizing the spine and facilitating fusion at various levels of the spine. In one type of system, a rod is disposed longitudinally along the length of the spine in the region of concern. The rod is arranged according to the anatomy and the correction desired. In this system, the rod is aligned along the spine and engages various vertebrae along its length. The rod engages, or more typically the parallel rods engage, the spine using fixation elements, such as, anchors attached to vertebral bodies by a bone screw.

Correction frequently require aligning the rod and screw at various angles along the length of the portion of correction. In order to provide this alignment, polyaxial screws/anchors have been developed. Many variations of polyaxial screw and rod fixation systems exist on the market today. Implanting the screws, anchors, and rods as can be appreciated typically requires a relatively large incision and dissection of the skin and muscle of the patient resulting in increased recovery, surgical trauma and the like.

Accordingly, to reduce for example surgical trauma, there is a need for a screw and rod fixation system that provides a strong, effective, and secure lock of the screw and rod in the desired position and angle that can be implanted using minimally invasive systems.

BRIEF DESCRIPTION OF THE DRAWING

The accompanying drawings illustrate various embodiments of the present invention and are a part of the specification. The illustrated embodiments are merely examples and illustrations of the present invention and do not limit the scope of the invention.

DETAILED DESCRIPTION

Figure 1:
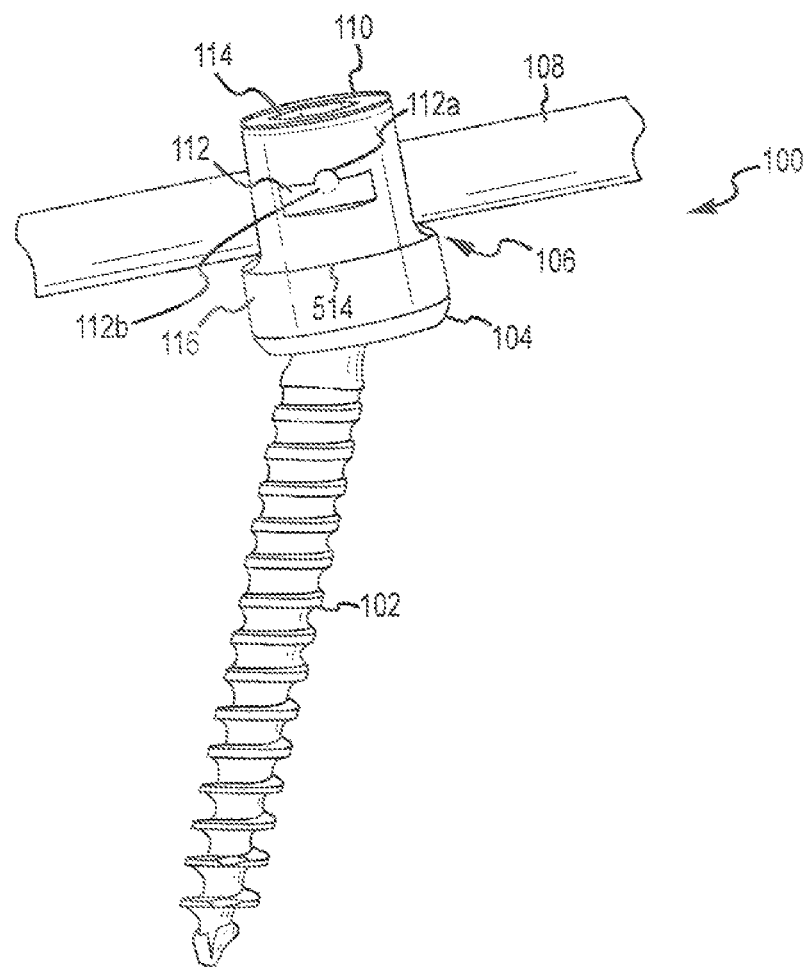
FIG. 1 shows a perspective view of a screw and rod fixation system in accordance with an embodiment of the present invention.

Referring now to FIG. 1, and in accordance with certain embodiments of the present invention, a screw and rod fixation system 100 is shown. FIG. 1 shows a perspective view of system 100. System 100 includes a bone screw 102, a housing 104 having an outer surface 106, a rod 108, and a compressive member 110, such as, a setscrew. Housing 104 may contain one or more first mating surfaces 112. First mating surfaces 112 are designed to mate with a tool (described further below). First mating surfaces 112 may include an alignment ridge 112a, which also may be a dimple, detent, protrusion, rib, or the like. Alignment ridge 112a conversely may be an alignment channel 112b as shown in phantom. Also, setscrew 110 typically has one or more second mating surface 114 to mate with a tool (not specifically shown but generally understood in the art). As shown in FIG. 1, first mating surfaces 112 are actually slots on an outer surface 106 of housing 104. While shown as slots, first mating surfaces 112 may be any number of designs including one or more dimples, hex detents, or other equivalent mechanisms as are known in the art. Second mating surface 114 is shown with a hex shape to accept a hex driver useful in threading the setscrew. Of course, one of ordinary skill in the art would recognize other and equivalent first and second mating surfaces 112, 114 are possible.

Figure 2:
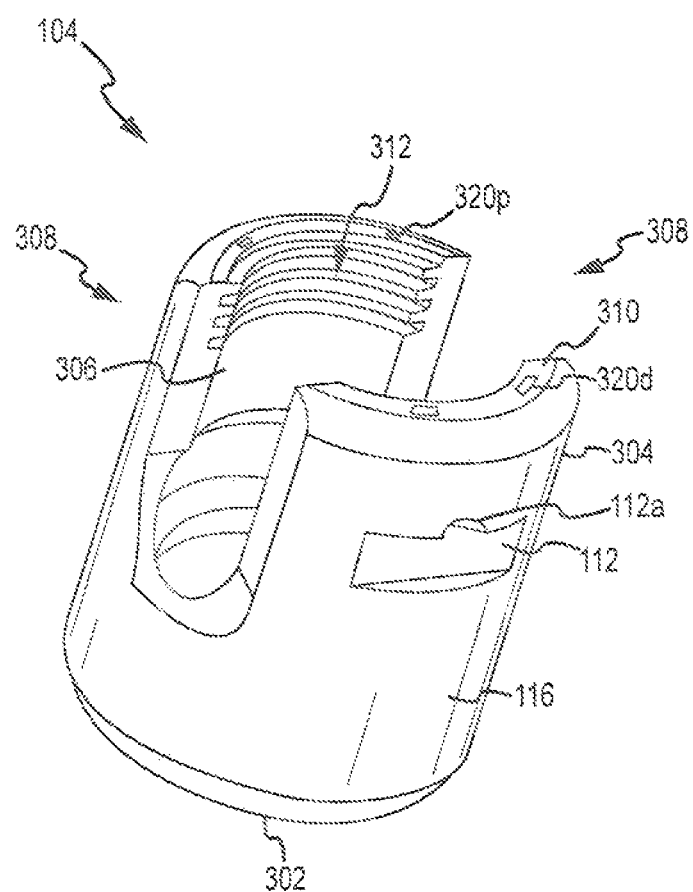
FIG. 2 shows a perspective view of a housing associated with an embodiment of the present invention shown in FIG. 1.

Referring now to FIG. 2, housing 104 is described in more detail. Housing 104 may be referred to as a coupling device, seat, or anchor. Housing 104 has a bone facing surface 302, at least one sidewall 304 having an outer surface 106 and an inner surface 306 (best seen in FIG. 2), first mating surfaces 112, a pair of opposed slots 308 in sidewall 304, a top edge 310, and a through hole 312 extending from top edge 310 to bone facing surface 302. Top edge 310 may have alignment points 320, which will be explained in more detail below. Alignment points 320 may be protrusions (as shown by 320p) or detents (as shown by 320d) as a matter of design choice, but it is believed detents would provided a lower profile.

The housing 104 is shown with one cylindrically shaped sidewall 304. It is believed providing housing 104 as a cylindrical shape reduces the profile of the device, but other shapes are possible, such as cubic or the like. If housing 104 had multiple sidewalls 304, the edges between the multiple sides should be beveled or rounded to inhibit tissue trauma.

Figure 3:
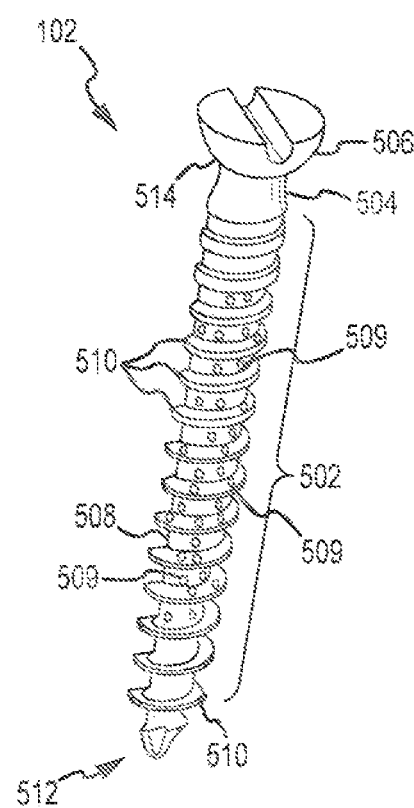
FIG. 3 shows a perspective view of a bone screw associated with an embodiment of the present invention shown in FIG. 1.
Figure 4:
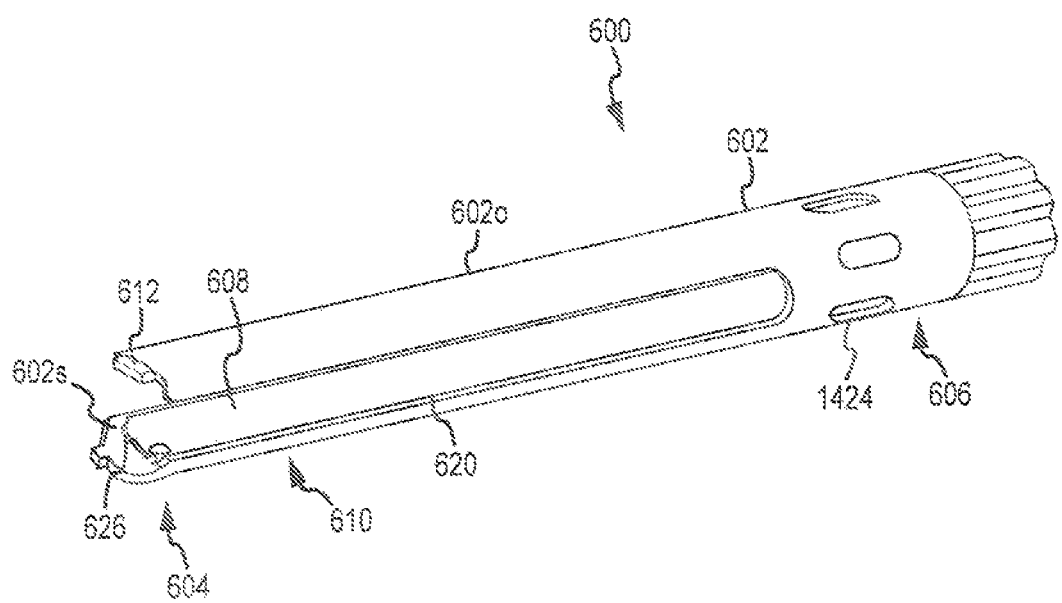
FIG. 4-7 show a tool useful for implanting the screw and rod system.
Figure 5:
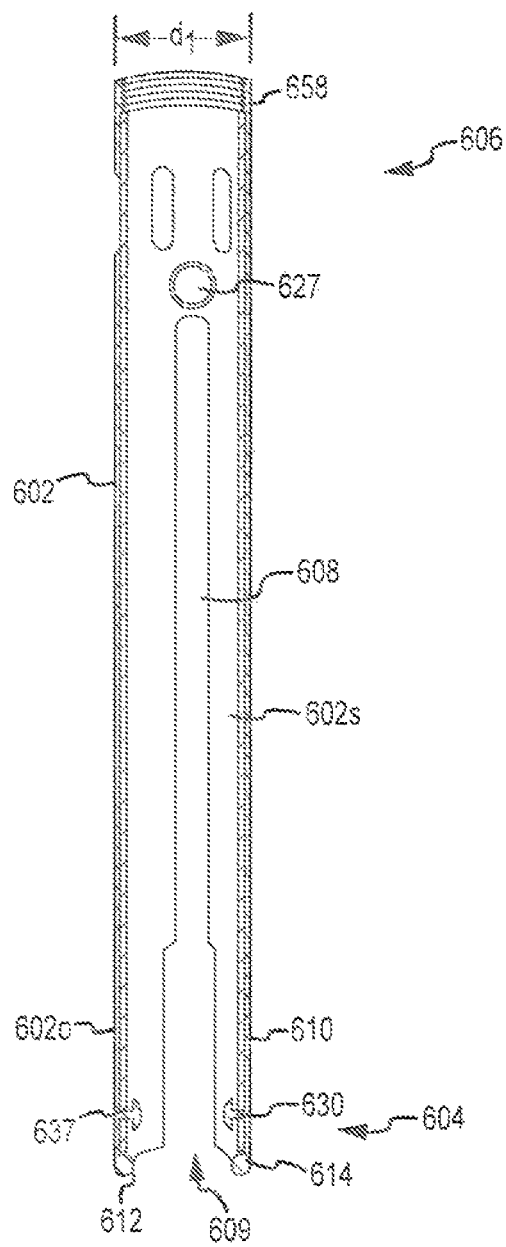
Figure 6:
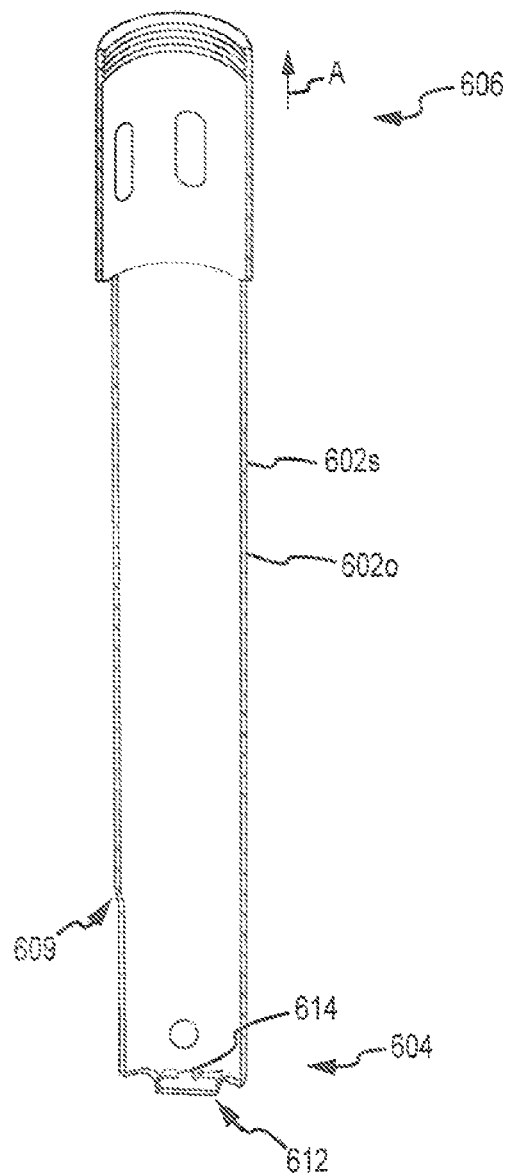
Figure 7:
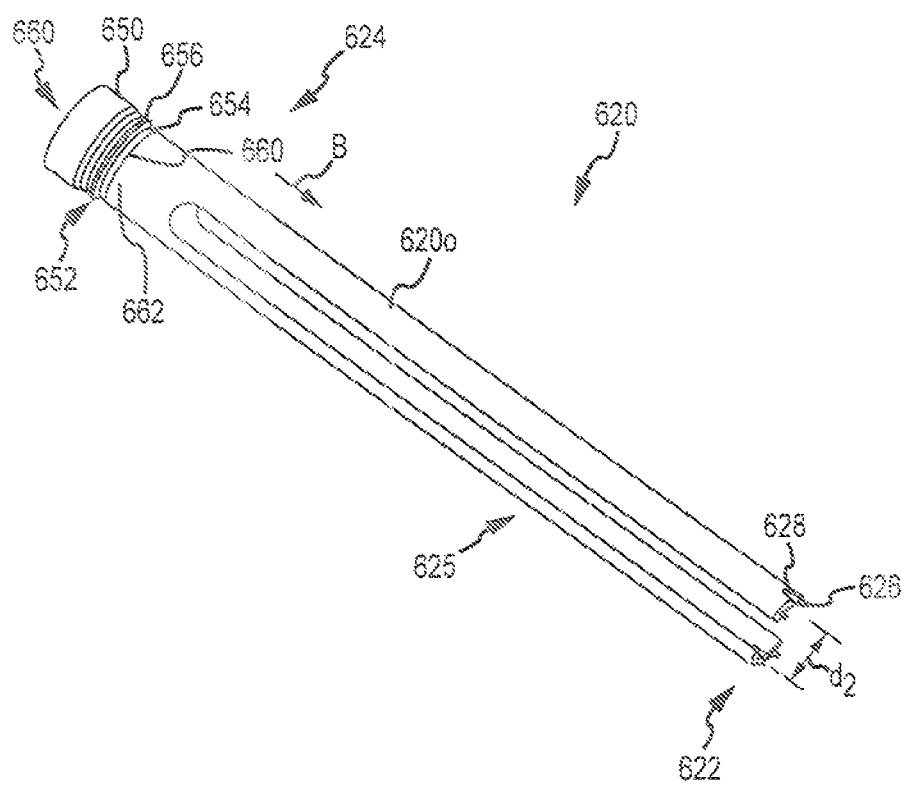

Bone screw 102 will now be described with reference to FIG. 3. While a particular bone screw 102 is described for completeness, any conventional bone screw is usable with the technology of the present invention. Bone screw 102 has a threaded portion 502, a transition portion 504, and a head portion 506. Threaded portion 502 can use any conventional thread, but as shown, threaded portion 502 has a shaft 508 and threads 510 machined such that shaft 508 has an increasing diameter from the tip 512 to transition portion 504. Further, threads 510 become relatively thicker towards transition portion 504. Designing threaded portion 502 in this fashion increases the frictional engagement of bone screw 102 in bone and generally increases the screw strength. To facilitate fusion between screw 102 and the bone, bone growth channels 509 may be provided in shaft 508, thread 510, or a combination thereof. It is believed micro-channels 509 in thread 510 facilitates bone growth and fusion of the screw to bone.

Transition portion 504 comprises the portion of bone screw 102 between threaded portion 502 and head portion 506. Transition portion 504 could be integrated into threaded portion 502. Transition portion 504 may be straight, curved, bowed, flared, or the like to transition threaded portion 502 to head portion 506.

Head 506 is shown with a convex outer surface 514 to cooperatively engage a corresponding concave surface in housing 104, not specifically shown by generally understood in the art. The convex outer surface 514 being designed to cooperatively engage the concave surface in housing 104 allows for polyaxial orientation of bone screw 102 with respect to housing 104. Head 506 is shown as a conventional flat head screw with a slot 516 to receive a tool, such as a screw driver. Rotation of the tool while engaged with slot 516 drive bone screw 102 into the associated bone. While shown as a flat head having a convex outer surface, other conventional bone screws are possible as are generally known in the art, such as, for example, heads with a more spherical shape, heads with a hex driver mating surface, heads with a fixed orientation with respect to housing 104, or the like.

Referring now to FIGS. 4-8, a tool 600 is provided to facilitate implanting the above described screws and rods. Tool 600 would typically be inserted through the skin of a patient after sufficient dilation. Tool 600 comprises a series of sleeves that will be explained in turn. Tool 600 includes a first, outer sleeve 602, sometimes referred to first or outer. First sleeve 602 has an inner surface 602s and an outer surface 602o. Inner surface 602s defines a first sleeve diameter $d_1$. First sleeve 602 includes a distal end 604 releasably connectable to housing 104 at first mating surfaces 112, as will be explained further below. First sleeve 602 has a proximate end 606 residing external to the patient. Extending from distal end 604 towards proximate end 606 are slots 608 separating tabs 610. Slots 608 include a flared portion 609. Flared portion 609 increases the flexibility or elasticity of tabs 610, which is useful in connecting first sleeve 602 to housing 104. Tabs 610 include first tool mating surface 612 to engage first mating surfaces 112 on housing 104. Rotating first sleeve 602 causes housing 104 to cause tabs 610 to expand. As first sleeve 602 is rotated, first tool mating surfaces 612, which are shown as protrusions, slide into first mating surfaces 112, which are shown as detents or grooves. Flexible tabs 610 collapse towards each other allowing outer sleeve 602 to grip housing 104 when first tool mating surface 612 align with first mating surfaces 112. First mating surface 612 optionally may be provided with an alignment dimple 614 to mate with alignment ridge 112a.

A second or inner sleeve 620 is provided to slidingly engage outer sleeve 602. Second sleeve 620 has a second outer surface 620o defining an second diameter $d_2$ which is less than $d_1$ and allows second sleeve to fit inside first sleeve in a sliding relation. Second sleeve 620 comprises distal end 622 and proximate end 624. Distal end 622 includes alignment portions 626 (which may be protrusions 626p (as shown) to mate with alignment detents 320d or which may be alignment detents 626d to mate with alignment protrusions 320p). Alignment portion 626 mate with corresponding alignment points 320 along top edge 310 of housing 104.

Second sleeve 620 includes at least one, but as shown two, alignment channels 628. Alignment channel 628 are shown opposite each other but could be otherwise configured. First sleeve 602 has at least one, but as shown two, corresponding alignment tabs 630 attached to an inner surface 602s. Alignment channel(s) 628 and alignment tab(s) 630 are matched such that when second sleeve 620 is slidably received in first sleeve 602, alignment tab(s) 630 move along and engage alignment slot(s) 628 to facilitate mating alignment portion 626 with alignment point 320. Second sleeve 620, optionally, may include one or more alignment tracks 625. Alignment tracks 625 fittingly engage with alignment ridge 627 (shown in FIG. 5) to facilitate alignment points 320 aligning with alignment portions 626 and alignment channels 628 aligning with alignment tabs 630.

Once slid into place second sleeve is rotationally locked to housing 104 by alignment portions 626 and alignment points 320 and rotationally locked to the first sleeve by alignment channels 628 and alignment tabs 630. Thus, second sleeve 620 acts as a strengthening member to inhibit torque from causing first sleeve 602 to twist off of housing 104 while driving, for example, bone screw into bone. To facilitate the connection, pin alignment tabs 630 may have a flared surface 637. Moreover, alignment channels 628 may be tapered to pinch or grasp tabs 630.

Once second sleeve 620 is slidably inserted into first sleeve 602, a connector 650 couples the proximate ends of the sleeves 602 and 620 together. In this exemplary embodiment, connector 650 causes first sleeve 602 and second sleeve 620 to clamp and lock to housing 104. For example, connector 650 may have a shaft 652 with outer surface 654 having threads 656. Inner surface 602s of first sleeve 602 at the proximate end would have corresponding threads 658. Shaft 652 would have a pushing surface 660 that abuts a proximate edge 662 of second sleeve 620. Threading connector 650 onto corresponding threads 658 pulls first sleeve 602 in direction A and pushes second sleeve in a direction B, opposite direction A by causing pushing surface 660 to push down on proximate edge 662. The relative forces between first sleeve 602 and second sleeve 620 clamps first sleeve 602 and second 620 to housing 104. In this exemplary embodiment, first tool mating surface 612 to applies a force against first mating surfaces 112 in direction A and the distail edge of second sleeve 620 applies a force against top edge 310 of housing 104 providing a clamping force. Connector 650 may have a tool mating surface 660 to allow a tool to thread the connector 650 to and from first sleeve 602.

Once connected, a bone screw drive can be inserted through second sleeve 620 to thread bone screw 102 into the bone. First and second sleeve 602 and 620 provide counter torque to allow driving the screw.

While the invention has been particularly shown and described with reference to an embodiment thereof, it will be understood by those skilled in the art that various other changes in the form and details may be made without departing from the spirit and scope of the invention.

I claim:

1. A method of attaching a tool to an implant to facilitate minimally invasive surgical procedures, the method comprising the steps of:

providing a tool comprising an inner sleeve having first and second elongate portions, each of the first and second elongate portions having a distal end and a proximal end, the inner sleeve having first and second slots extending between the first and second elongate portions from the distal ends thereof, the first and second slots each having a slot length greater than one half of a length of the first and second elongate portions;

an outer sleeve comprising third and fourth elongate portions, each of the third and fourth elongate portions having distal and proximal ends, the outer sleeve member further comprising third and fourth slots extending between the third and fourth elongate portions from the distal ends thereof, the third and fourth slots each having a length greater than one half the length of the third and fourth elongate portions, wherein the inner sleeve is sized to be received within the outer sleeve, a connector member adapted to couple the proximal ends of the first and second elongate portions with the proximal ends of the third and fourth elongate portions, respectively;

an alignment feature adapted to align the first slot with the third slot, and to align the second slot with the fourth slot, when the inner sleeve is received within the outer sleeve, wherein the alignment feature comprises at least one alignment channel located at the distal end of one of the first and second elongate portions, and at least one alignment projection located on a radial inner surface proximate the distal end of one of the third and fourth elongate portions and configured to selectively lock with the at least one alignment channel; and an implant engagement feature disposed on a distal end of the third elongate member, the implant engagement feature adapted to releasably secure the second sleeve to the implant;

inserting the distal ends of the third and fourth elongate portions through an incision until the distal ends are proximate the implant;

coupling the distal ends of the third and fourth elongate portions to the implant using the implant engagement feature;

sliding the inner sleeve inside the outer sleeve such that the first and second elongate portions move along the third and fourth elongate portions until a first alignment portion disposed on the distal end of at least one of the first and second elongate portions engages a second alignment portion disposed on an uppermost edge of the implant; and moving a part of the implant along the slot and between the first and second elongate portions until the part of the implant is implanted at a surgical site.

2. The method of claim 1, wherein sliding the inner sleeve comprises locking the tool to the implant.

3. The method of claim 1, wherein the implant engagement feature comprises a projection extending from the third elongate member distal end, wherein the step of coupling the third and fourth elongate members comprises rotating the outer sleeve until the projection engages the implant.

4. The method of claim 1, wherein the step of moving a part of the implant along the slot comprises moving the part from the proximal end to the distal end.

5. The method of claim 1, further comprising coupling the first and second elongate members with the third and fourth elongate members.

6. The method of claim 1, wherein the first alignment portion includes one of a projection and a detent, and the second alignment portion includes the other of the projection and the detent, and wherein the step of sliding the inner sleeve includes mating the one of the projection and the detent with the other of the projection and the detent.

7. The method of claim 1, wherein the implant includes a pedicle screw anchor, and wherein coupling the distal ends of the third and fourth elongate portions to the implant includes engaging the implant engagement feature with a radially outer surface of the pedicle screw anchor.

8. The method of claim 7, wherein the implant engagement feature includes a protrusion and an alignment ridge, and the radially outer surface includes a detent and an alignment dimple, the alignment dimple disposed between the detent and the uppermost edge of the implant, the method further comprising:

mating the protrusion with the detent; and
mating the alignment ridge with the alignment dimple.

\* \* \* \* \*